United States Patent [19]
Mathewson et al.

[11] Patent Number: 5,316,724
[45] Date of Patent: May 31, 1994

[54] MULTIPLE BLOOD PATH MEMBRANE OXYGENATOR

[75] Inventors: Wilfred F. Mathewson, Dana Point; Richard L. Bringham, San Clemente; Philip L. Ritger, El Toro; David Karshmer, Redwood City, all of Calif.

[73] Assignee: Baxter International Inc., Deerfield, Ill.

[21] Appl. No.: 945,998

[22] Filed: Sep. 15, 1992

Related U.S. Application Data

[60] Continuation of Ser. No. 794,318, Nov. 14, 1991, abandoned, which is a division of Ser. No. 331,479, Mar. 31, 1989, abandoned.

[51] Int. Cl.$^5$ .............................................. A61M 1/14
[52] U.S. Cl. ...................................... 422/48; 422/45; 128/DIG. 3
[58] Field of Search ............. 422/45, 48; 128/DIG. 3; 261/DIG. 28; 55/16, 158; 210/321.8, 321.89, 498

[56] References Cited

U.S. PATENT DOCUMENTS

| | | | |
|---|---|---|---|
| 4,261,951 | 4/1981 | Miley | 422/46 |
| 4,306,018 | 12/1981 | Kirkpatrick | 435/2 |
| 4,376,095 | 3/1983 | Hasegawa | 422/46 |
| 4,424,190 | 1/1984 | Mather et al. | 422/46 |
| 4,639,353 | 1/1987 | Takemura et al. | 422/48 |
| 4,657,743 | 4/1987 | Kanno | 422/46 |
| 4,659,549 | 4/1987 | Hamada et al. | 128/DIG. 3 |
| 4,698,207 | 10/1987 | Bringham et al. | 422/46 |
| 4,715,953 | 12/1987 | Leonard | 210/321.8 |
| 4,722,829 | 2/1988 | Giter | 422/46 |
| 4,732,673 | 3/1988 | Dagard et al. | 55/158 |
| 4,749,551 | 6/1988 | Borgione | 422/48 |
| 4,791,054 | 12/1988 | Hamada et al. | 310/321.8 |

FOREIGN PATENT DOCUMENTS 0176651 2/1985 European Pat. Off. .
139562 12/1986 Japan .

Primary Examiner—James C. Housel
Assistant Examiner—Lien Tran
Attorney, Agent, or Firm—Raymond Sun; Bruce M. Canter

[57] ABSTRACT

A membrane oxygenator designed to provide blood flow evenly across a gas permeable membrane in a direction substantially perpendicular to the longitudinal direction of the gas permeable membrane. In particular, the present invention is directed to a membrane oxygenator wherein the blood is distributed substantially evenly and at a substantially constant velocity, in a cross-wise direction across the gas permeable membrane. In accordance with a preferred embodiment, the membrane is a bundle of gas permeable hollow fibers with the blood being distributed in a direction substantially perpendicular to the longitudinal direction of the individual hollow fiber membranes.

16 Claims, 3 Drawing Sheets

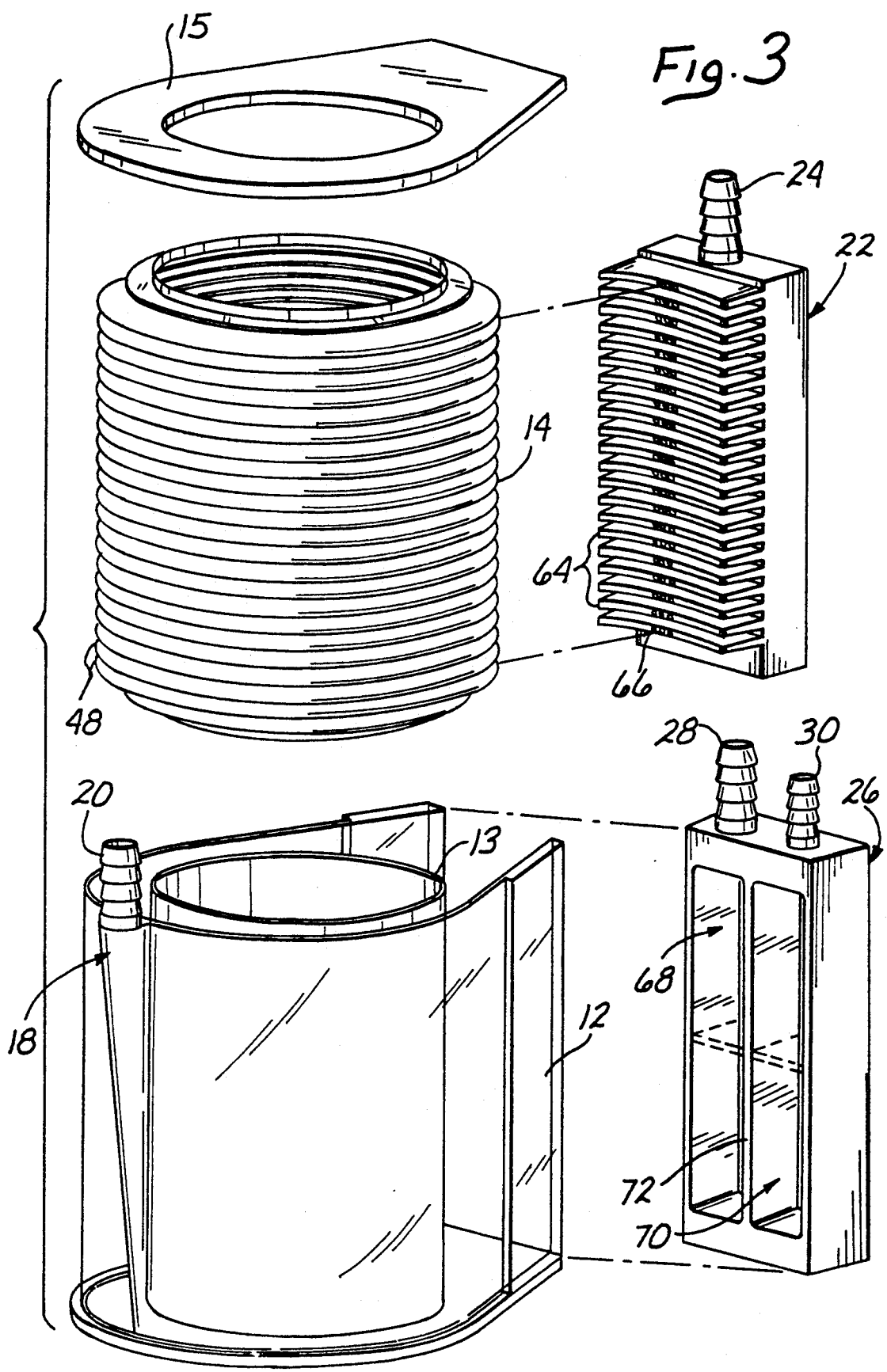

MULTIPLE BLOOD PATH MEMBRANE OXYGENATOR

RELATED CASES

This application is a continuation of U.S. application Ser. No. 07/794,318, filed on Nov. 14, 1991, which is a divisional of U.S. application Ser. No. 07/331,479, filed on Mar. 31, 1989, both of which have been abandoned.

BACKGROUND OF THE INVENTION

The present invention is directed to devices and methods for oxygenating blood during surgery, and in particular, to membrane oxygenators.

Devices which oxygenate blood are typically used in surgical operations where the supply of blood from the heart is interrupted, e.g. during open heart surgery, or any other surgery performed on the heart or lungs. Oxygenation devices fall generally into two different categories, bubble and membrane oxygenators.

For reason not to be discussed herein, membrane oxygenators have recently become preferred over bubble oxygenators. Membrane oxygenators include a membrane with which the blood is brought into direct contact. Commercially available membrane oxygenators utilize hollow tubing or fibers which are formed from a material through which gas may diffuse under the proper operating conditions, without an appreciable passage of fluid. The blood is either passed through the tubing or fibers, with an oxygen bearing gas passed about the fibers, or conversely the blood can be passed about the tubing or fibers with the oxygen bearing gas passed there through. The tubing or the hollow fibers may be formed from silicon, e.g. silicon tubing, or be formed as a porous fiber from a hydrophobic polymeric material.

Examples of various types of membrane oxygenators are disclosed in U.S. Pat. No. 4,261,951, issued to Milev on Apr. 14, 1981; U.S. Pat. No. 4,376,095, issued to Hasegawa on Mar. 8, 1983; U.S. Pat. No. 4,424,190, issued to Mather, III et al, on Jan. 3, 1984; and U.S. Pat. No. 4,657,743, issued to Kanno on Apr. 14. 1987, and European Patent Application Number 176,651, filed by Mitsubishi Rayon Co. Ltd, on Feb. 14, 1985.

The gas exchange rate for an oxygenator is determined by multiplying the mass transfer constant for that specific oxygenator times the partial pressure of oxygen, times the total gas exchange surface area. The mass transfer constant is dependent upon the material from which the membrane is formed, the porosity of the membrane, and the operating characteristics of the oxygenator, that is, the manner in which the blood is passed across the membrane. The mass transfer constant is fixed for each type of oxygenator. While the partial pressure of oxygen can be altered to affect gas transfer, it can not exceed one atmosphere and is usually fixed for each type of oxygenator. Thus, the only variable which can be altered to effect the overall gas exchange rate for a given oxygenator is the total gas exchange surface area.

It is thus evident that in order to increase the gas exchange capabilities for a specific oxygenator, its size must be increased. While this allows for a greater gas exchange, the resulting oxygenator may suffer other drawbacks. For example, the larger the oxygenator the greater the priming volume. The priming volume is that amount of fluid necessary to fill the oxygenator. Generally, it is desirable to minimize the priming volume which reduces the gas exchange surface area, while designing an oxygenator with a higher mass transfer constant.

To a certain degree the material from which the membranes are formed, as well as the dimension and porosity of such membranes, may be controlled to improve the mass transfer constant. Altering the operating characteristics of an oxygenator has the greatest effects upon the mass transfer constant. Generally, this involves altering the manner in which the blood is passed across the membranes.

Some blood oxygenators provide that the blood will flow in a direction substantially equivalent to the axis of the hollow fibers, see U.S. Pat. No. 4,698,207, issued to Bringham et al on Oct. 6, 1987. This is a result of directing the blood either through the fibers, or in a direction generally equivalent to the orientation of the hollow fibers. The basic disadvantage with this type of construction is the inefficiency in performing the oxygenation as blood flows across the membrane.

Other blood oxygenators attempt to direct the blood across the width of the fibers, see U.S. Pat. No. 4,424,190, issued to Mather, III et al on Jan. 3, 1984. The oxygenator disclosed in this reference incorporates an internal porous cylindrical core 68 about which is positioned a plurality of hollow fibers. The core is formed with numerous openings orientated in a direction generally perpendicular to the hollow fibers. The core and fibers are positioned within an outer cylindrical wall 66, with gas directed through the individual hollow fibers. Blood enters core 68, and exits out through the openings in a direction generally perpendicular to the bundle of hollow fibers. The direction of blood flow through the device taught in Mather III, et al provides for a better degree of oxygenation than obtained with those devices which pass the blood in substantially the same direction as the axis of the hollow fibers. However, the flow obtained by the device taught in Mather III, et al is uneven, and tends to become concentrated in certain portions of the fiber bundle.

An integrated blood oxygenator and heat exchange device is disclosed in a recently published Japanese patent application, publication number 1988-139562 which was published Jun. 11, 1988. The blood oxygenator includes a central heat exchange core which is formed with laterally disposed folds, that is folds arranged between the core ends. Numerous hollow threads are wrapped about the heat exchange core. These threads are laid either parallel to the core axis or piled one by one diagonally across the core. The blood is directed into the core folds and then passes out through the fibers. There is no commercially available embodiment of the disclosed device which would allow for a direct comparison of the gas exchange rate.

There thus remains the need to provide a membrane oxygenator having an improved efficiency in the exchange rate for oxygen.

SUMMARY OF THE INVENTION

The present invention is directed to a membrane oxygenator designed to provide blood flow evenly across a gas permeable membrane in a direction substantially perpendicular to the longitudinal direction of the gas permeable membrane. In particular, the present invention is directed to a membrane oxygenator wherein the blood is distributed substantially evenly, and at a substantially constant velocity, in a cross-wise direction across the gas permeable membrane. In accordance with a preferred embodiment, the blood is distributed in a film in a direction substantially perpendicular to the longitudinal direction of the membranes.

The preferred oxygenator includes a housing in which is disposed a body formed for defining a plurality of individual blood flow pathways. Each blood flow pathway has associated therewith at least a first gas permeable membrane which defines a gas flow pathway separate from the blood flow pathway. The gas permeable membrane is further formed with passages oriented in a direction substantially perpendicular to the longitudinal direction of the membrane. These passages are formed to allow for the passage of blood out from the blood flow pathway, preferably after the blood flow pathway has become substantially filled with blood. These gas permeable membrane passages are preferably dimensioned to receive a thin layer or film of the blood from the blood flow pathway.

In accordance with another preferred embodiment, the membrane oxygenator includes a housing in which is mounted a cylindrical core. This core is formed with a plurality of channels about its outer surface. These channels define the individual blood flow pathways. The oxygenator further includes a plurality of gas permeable membranes, in the form of individual porous hollow fibers, situated in each of the channels. Each hollow fiber membrane defines a gas flow pathway separate from the blood flow pathway. The hollow fiber membranes are arranged in the blood flow pathways to allow for the flow of blood between adjacent ones of the fibers in a direction substantially perpendicular to the longitudinal direction of the fibers. A blood manifold is provided for delivering the blood directly into the individual blood flow pathways, and a gas manifold is provided for delivering an oxygen bearing gas through to the hollow fibers.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 3 is an exploded view of the device of FIG. 1;

DESCRIPTION OF THE PREFERRED EMBODIMENTS

Figure 1:
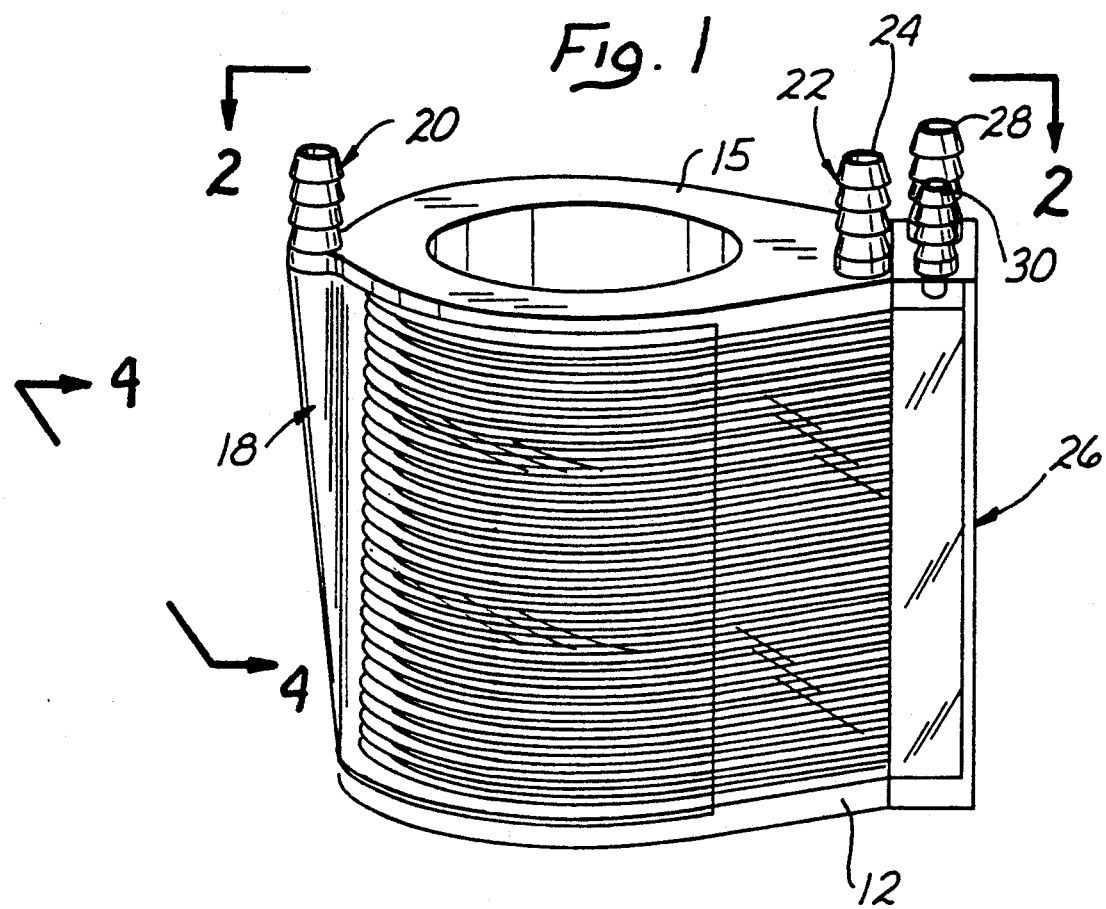
FIG. 1 is a prospective side view of a blood oxygenator in accordance with an embodiment of the invention.

The present invention is directed to a device which oxygenates blood during surgical procedures, that is a device which performs the transferring of oxygen for carbon dioxide in blood. The reasons for performing this oxygenation during such operations as open heart surgery are well known.

The device of the invention includes a housing which encloses a support core. This core is formed with an external surface upon which is disposed a plurality of adjacently located blood receiving channels. Each of these channels define a blood flow pathway. The blood flow pathways, as defined by the channels, may be integrally formed in the surface of the support core, e.g. by forming the body's surface with grooves or other types of undulations, or by affixing separately formed channels to the external surface of the support core. In accordance with a preferred embodiment, the channels are arranged in a substantially parallel orientation about the external circumference of the support core.

The device of the invention further includes at least one gas permeable membrane partially positioned in each of the blood receiving channels. For the purpose of the present invention the term "gas permeable membrane" is meant to include substrate formed from a material which functions to allow for the transfer or diffusion of oxygen and carbon dioxide from one side of the substrate to the other, without any appreciable passage of fluids. These types of membranes will allow oxygen to pass from an oxygen bearing gas to the blood, which is oxygen deficient, while allowing for the transfer of carbon dioxide from the blood to the gas without appreciable passage of fluid.

Membranes useful for the practice of the invention include those formed from silicone, polyolefin, e.g. polypropylene or polyethylene, or other suitable hydrophobic polymeric material, including, without limitation, composite membranes, porous or non-porous membranes, or symmetric or asymmetric membranes. Such membranes may be in the form of flat structures, corrugated sheets, tubular structures, or hollow fibers.

Furthermore, such membranes should define a gas passageway separate from the blood flow pathways, as defined by the channels. The preferred membranes are of the porous hollow fiber type, with the gas or blood pathway being through the interior of the fiber. For a more detailed description of such membranes, and theory of operation, see "Cardiopulmonary Bypass". 2nd Edition, Charles C Reed and Trudi B. Stafford, Texas Medical Press, Inc, 1985, Chapter 28 "Membrane Oxygenator", pages 427–449, which description with respect to such membranes is incorporated herein by reference.

The types of hollow fiber membranes useful for the practice of the invention are well known, with such membranes described in any one of the above mentioned U.S. patents issued to Mather III et al, Kanno, Hasegawa and Leonard. All such relevant disclosures to such membranes are incorporated herein by reference.

At least one hollow fiber membrane is partially positioned in each of the individual blood receiving channels. In accordance with a more preferable embodiment, a plurality of individual hollow fiber membranes are positioned in each channel. The precise number of hollow fibers is dependent upon the size of the respective channel, the size of the hollow fiber membranes and the desired rate or efficiency of gas exchange. That is, the total surface area for the membrane may be increased by using a larger number of smaller dimensioned hollow fibers.

A plurality of individual blood oxygenation pathways are formed on the surface of the core bodies. Each blood flow pathway is defined by the exposed surface of the individual blood receiving channel and the external surface of the membranes positioned in the respective channel. The device further includes a mechanism for delivering blood into each of the channels, so that the blood will flow into, and substantially fill the channel.

Referring now to FIGS. 1-4, a specific embodiment of the invention will now be described in greater detail. The membrane oxygenator of the invention is seen generally at 10. This device 10 will be connected in an extracorporeal circuit for the purpose of performing the necessary gas exchange. The device 10 generally includes an outer housing enclosure 12, which has a support core 13 about which is mounted a bellows 14.

Figure 2:
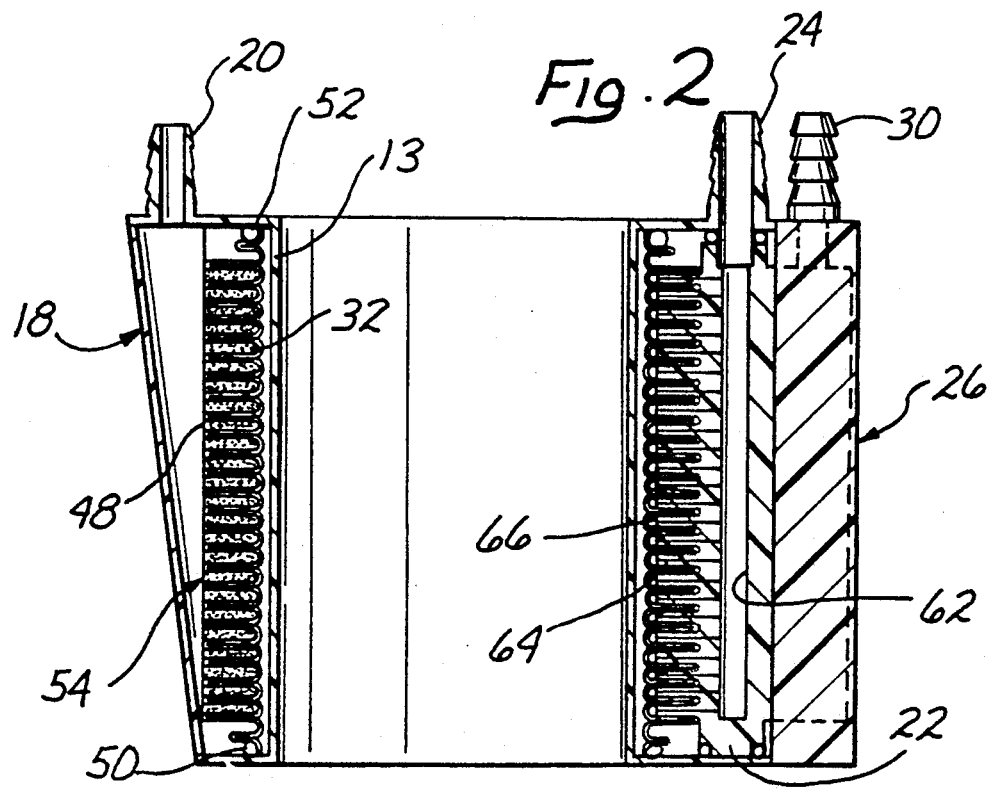
FIG. 2 is a cross-sectional view of FIG. 1 along line 2—2.
Figure 2A:
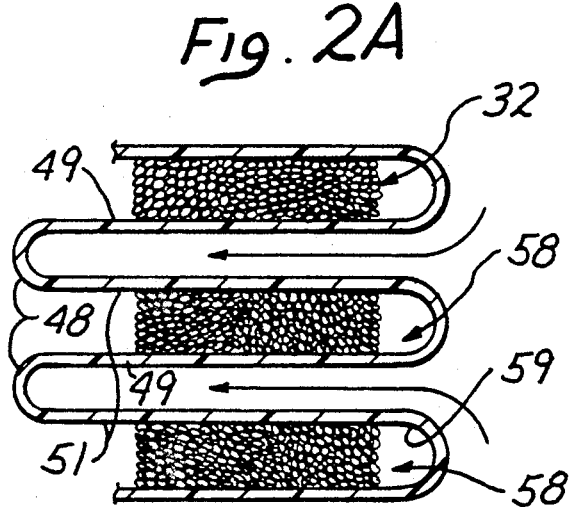
FIG. 2A is an enlarged view of the blood receiving channels, as defined by the pleats of the bellows and the hollow fiber membranes, as seen generally in FIG. 2.

The bellows 14 is farmed with a plurality of pleats 48, with a blood receiving channel 58 defined between each of the adjacently positioned pleats 48, such channels 58 best seen in FIG. 2A at 58. The illustrated blood receiving channels 58 are arranged about the circumference of the cylindrically shaped bellows 14 in a substantially parallel orientation. As will be described herein, blood is delivered to each of the channels 58 to place the blood into intimate contact with the hollow fiber membranes.

Blood enters the device 10 through a blood manifold, seen generally at 22, which is fitted into the housing enclosure 12. As will be described more fully herein, the blood manifold 22 is formed to deliver blood to the individual blood receiving channels 58. The manifold 22 also includes a blood inlet tubing connector 24 to which a suitable tubing, not shown, is coupled for delivering blood to the device 10 from the patient.

The housing enclosure 12 is also formed with a blood exit manifold 18, and exit tubing connector 20. The blood will pass out of the blood receiving channels, about the individual hollow fibers, into the exterior region of the housing enclosure 12. This blood will exit the housing enclosure 12 through the exit manifold 18 and the tubing connector 20. A tube, not shown, coupled to the tubing connector 20, will direct the blood back to the patient, or to another device in the extracorporeal circuit, not shown.

The device 10 further includes a gas manifold 26. This gas manifold 26 may either be a separate structure mounted to the device housing enclosure 12, or integrally formed therewith, and is formed to deliver a gas, typically an oxygen bearing gas, i.e. either pure oxygen or blends of oxygen with other suitable gas, e.g. nitrogen, to the gas passage defined by the interior of the hollow fiber membranes. That is, a bundle of porous hollow fibers are arranged between adjacently positioned pleats of the bellows 14. These fibers, which are generally referenced at 32, are wrapped about the bellows 14, with the opposing open ends of each of the fibers 32 positioned contiguously along a side of the bellows 14, and embedded within a potting polymeric composition, seen at 60. The urethane potting material 60 may be selected from any suitable potting material, e.g. any of the urethane potting materials taught by the above incorporated references, and in particular the Leonard patent.

Figure 4:
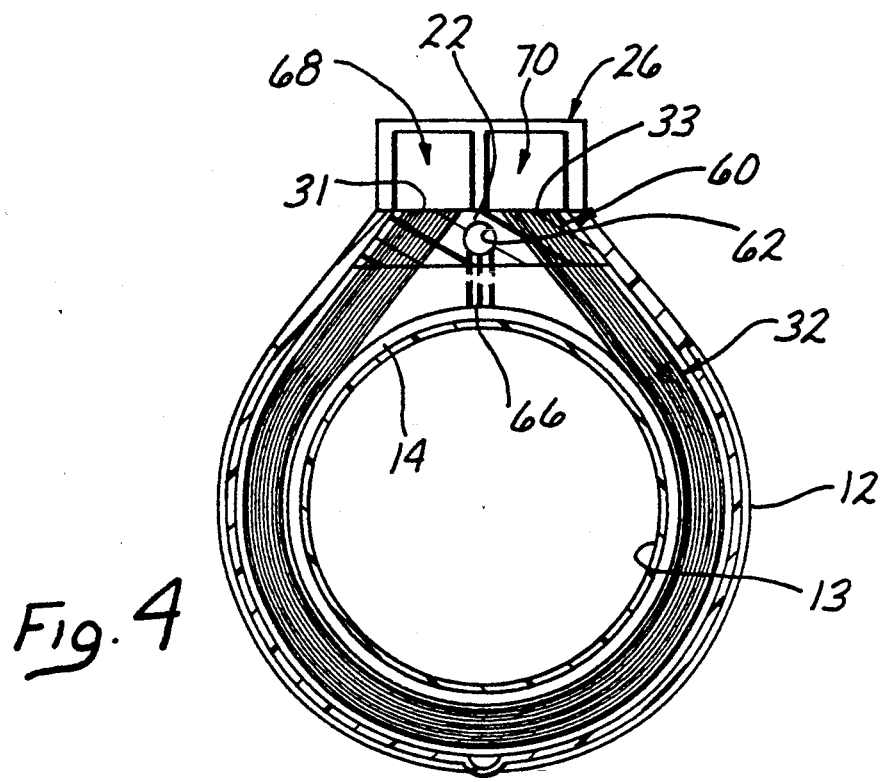
FIG. 4 is a cross-sectional view of FIG. 1 along line 4—4.

As stated, the opposite open ends of the fibers 32 are embedded within the potting material 60 to form two separate, but adjacently positioned linear arrays of open fiber ends, with such arrays or rows seen in FIG. 4 at 31 and 33. The respective individual fiber ends are exposed at a surface of the potting material to provide access into the fibers. Typically, after the fibers have been potted, a layer of the potting material, in which the fibers are embedded, is removed to expose the open ends of the individual fibers.

The gas manifold 26 is formed with two adjacent hollow compartments, seen at 68 and 70. When the manifold 26 is secured to the device 10, each of these compartments 68 and 70 is arranged over one of the rows 31 and 33, respectively. The manifold 26 further includes ports to introduce or receive gas from one of these compartments 68 or 70. The gas enters the fibers 32 through the open ends, and travels around the bellows 14 through such fibers to exit out the opposite open ends of the fibers 32 into the other compartment 68 or 70. The compartments 68 and 70, in combination with the individual fibers 32, define a plurality of separate gas flow pathways around the bellows 14.

A more detailed description of the various components of the device 10 will now be discussed with reference to FIGS. 2, 3 and 4. As stated the device 10 is an assembly of the bellows 14, positioned about the central core 13, which is nested in the housing enclosure 12. A cover plate 15 is then fitted on the housing 12. As stated, these components are dimensioned to ensure a snug fit. The device 10 is sealed at the junction between the bellows 14 and the housing enclosure 12 by O-rings which are wedged between such components, such rings seen generally at 50 and 52. The housing enclosure 12 and bellows 14 may be secured together by any suitable means, e.g. by being bolted together, or more preferentially by a suitable adhesive. The bellows 14 is formed with multiple pleats 48. Each of the pleats 48 is defined by two walls, seen generally at 49 and 51. The outer surfaces of these walls 49 and 51 define the blood receiving channels 58.

The blood flow pathway is defined by the blood receiving channels 58, in combination with the gas exchange membrane defined by the fibers 32, with one of the blood flow pathway 59 best seen in FIG. 2A. The blood flow pathway 59 is seen as a gap between the fibers 32 positioned between adjacently positioned pleats 48, and the pleat walls 49 and 51. More specifically, the bundle of fibers 32 is positioned between adjacently positioned pleats 48 to provide for a gap between the innermost ones of the fibers and the pleats walls 49 and 51. The bundle of fibers 32 normally fills a majority of that portion of the area between the adjacent pleats 48, while providing for the defined gap. Preferentially, the fiber 32 bundle should fill from about forty percent to about sixty percent of the area between the adjacently positioned pleats 48.

As stated, the gas manifold 26 is formed with two compartments, seen respectively at 68 and 70. The gas manifold 26 is a generally rectangular shaped body with the individual compartments separated by a partition wall 72. The gas manifold 26 is mounted to the housing 12 contiguous with the urethane potting material 60. Each of the compartments 68 and 70 is positioned to selectively cover one of the rows 31 or 33 of the exposed fiber open ends. This arrangement defines a gas entrance and exit to the fibers 32, via a respective one of the compartments 68 and 70.

The gas manifold 26 is further formed with a gas inlet port 28 and a gas outlet port 30. These ports 28 and 30 communicate with the compartments 68 and 70, respectively. Gas is delivered into the device 10 by connecting a source of oxygen bearing gas to the gas inlet port 28 which delivers the gas to the compartment 68. The gas enters the compartment 68 entering the individual hollow fibers 32 through each of the exposed fiber open ends. The gas travels about the bellows 14 through the individual hollow fibers 32, and exits into the compartment 70 out from the opposite exposed fiber open ends.

The urethane potting material 60 not only fixes the fibers 32 in position, but also fixes the blood manifold 22 in the housing 12. The blood manifold 22, which is best seen in FIG. 3, is an elongated body formed with a centrally disposed conduit 62 running through its length, as best seen in FIG. 2. This conduit 62 is open at one end to the blood inlet tubing connector 24. The manifold 22 is further formed with a plurality of fingers 64 which extend outward from one side of the manifold 22. These fingers 64 are spatially separated from each other and have a generally rectangular shape. The fingers 64 are also dimensioned to snugly fit between the adjacently disposed pleats 48 of the bellows 14. This manifold 22 is fixed by the urethane potting material 60 to the bellows 14 between the two side-by-side hollow fiber rows 31 and 33.

As best seen in FIG. 4, each finger 64 is formed with one or more open passages, one of which is seen generally at 66. Each of these passages 66 communicates with the conduit 62, and with the associated blood flow pathway 59 when the respective finger 64 is fitted between the pleats 48. Blood entering the blood manifold 22 travels through the conduit 62, and selectively enters and flows through each of the passages 66. The blood will exit the passages 66 into the associated blood flow pathway 59. The blood will then travel through the individual blood flow pathway 59 about the bellows 14. As the gap defining the blood flow pathway 59 fills, the blood flows outwards, about the hollow fibers 32 disposed in the associated blood receiving channel 58.

As stated, the direction of the blood across the hollow fiber membranes is substantially perpendicular to the longitudinal direction of the hollow fibers, that is, perpendicular to the fiber axis. Furthermore, the hollow fibers are spatial separated to allow the blood to pass between such fibers as a relatively thin layer, generally, in the range of one to about five mils thickness.

As the blood flows about the individual hollow fibers 32, the exchange of gases occurs. This gas exchange is basically a diffusion process with oxygen diffusing from a higher concentration in the gas, through the fiber membrane into the blood, with carbon dioxide diffusing from a higher concentration in the blood, through the fiber membrane into the gas.

The importance of the flow characteristics oxygenator of the invention, and in particular the flowing of the blood about the individual hollow fibers, or for that matter any membrane, in a direction substantially perpendicular to the longitudinal direction of the membrane will now be described in greater detail with reference to FIG. 5.

Figure 5:
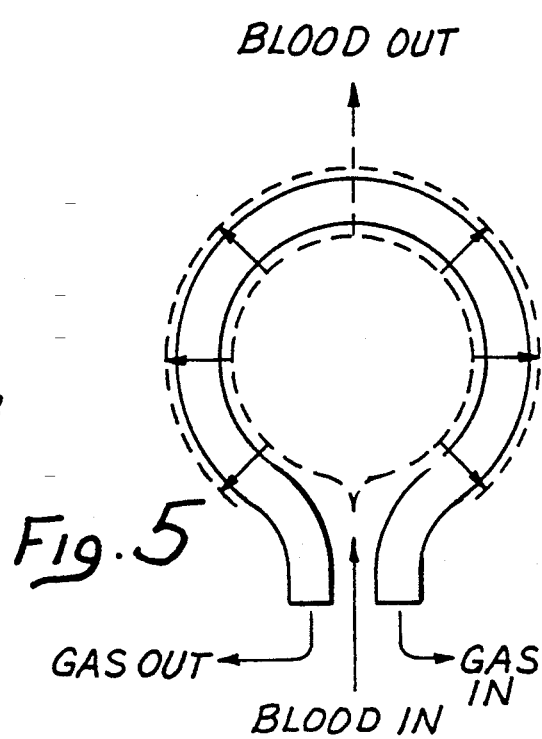
FIG. 5 is a schematic illustration of the blood and gas flow paths through the oxygenator seen in FIG. 1.

FIG. 5 is a schematic illustration of the flow path for the blood and gas through the oxygenator of the invention. As seen, the blood flow across the fiber membranes is in a direction generally referred to as a cross-flow. That is, blood enters the blood flow pathways 59, that is the blood receiving channels 58, from the blood inlet manifold 22. The blood then flows about the bellows 14 through the pathways 59, until the pathways 59 become substantially filled with blood. At this time, the blood passes out of the pathways 59, about and between the adjacently positioned ones of the individual hollow fiber membranes 32 in a direction substantially perpendicular to the orientation of the fibers 32.

The arrangement of the hollow fibers 32 in the blood receiving channels 58 also promotes distribution of the blood across the fibers 32 in a substantially even distribution, at a substantially constant velocity, which increases the overall efficiency of the gas exchange rate for the oxygenator of the invention in comparison to previous oxygenators. As is well known, the rate or efficiency of gas exchange for any oxygenator is dependent upon the mass transfer constant for that particular oxygenator, which is dependent upon the operating characteristics of the oxygenator and the permeability of the membrane, as well as the partial pressure of oxygen and the surface area of the membrane exposed to the blood. It is believed that the efficiencies achieved with the oxygenator of the invention is a result of the oxygenator's higher mass transfer constant. This higher mass transfer constant allows the oxygenator to achieve a higher gas exchange efficiency without the need to increase the surface area of the membrane which is exposed to the blood.

EXAMPLES

The following examples demonstrate that the oxygenator of the invention is more efficient in gas exchange than presently available oxygenators. In particular, the following examples compare the gas exchange rates of three commercially available oxygenators to an oxygenator prepared in accordance with the present invention. The commercial oxygenators included a Bentley CM-50, manufactured and sold by the Bentley Laboratories Inc subsidiary of the Baxter Healthcare Corporation., an oxygenator manufactured and sold by the Medtronic Corporation under the designation Maxima TM, and an oxygenator sold by the Sarns division of 3M under the designation .5MO. The blood flow path for both the 3M and Medtronic oxygenators was about the exterior of the hollow fibers, while the blood flow path for the CM-50 oxygenator was through the fibers.

The representative oxygenator of the invention used in the examples was actually a single blood flow pathway channel as defined above. A bundle of hollow fibers were positioned in this channel. The actual membrane surface area for each of these representative oxygenators is listed for the corresponding example. The estimates of pressure drop, surface area and priming volume were based on scaling factors.

The actual testing involved subjecting the oxygenators to a stress test. This stress test allowed for the calculation of the performance capabilities for each oxygenator. The stress test involved passing bovine blood through a gas exchange test circuit. This circuit had the following gas and blood inlet conditions for the bovine blood:

(1) gas source was pure oxygen (2) blood inlet parameters were $0+/-2$ microequivalents/liter of base excess (3) blood temperature of $37°$ C.$+/-0.5°$ C.

(4) blood hemoglobin of $11.5+/-0.2$ gram percent (5) blood carbon dioxide partial pressure of $45+/-2$ mmHg (6) blood venous (inlet) oxygen saturation of $45+/-1$ percent The flow rates of the blood through the circuit were selected to obtain an arterial (exit) oxygen saturation value of between 80% to about 98%, with the gas flow rates adjusted to maintain an equivalent blood and gas flow rate.

At least two examples were performed for each oxygenator, with each example consisting of numerous runs. The blood flow rate through the oxygenator was varied for each run. The corresponding blood flow rates in liters per minute (LPM) for each run are provided in the tables.

The blood oxygen saturation (in percent) for each run through the respective oxygenator was measured for the venous (inlet) using a co-oximeter, e.g. a co-oximeter designated as a IL-282 co-oximeter sold by Instrument Laboratories, Lexington, Mass. The blood oxygen saturation (in percent) for each run of the respective oxygenator was calculated for the arterial (outlet) using the blood outlet conditions of base excess, blood pH, blood temperature and the partial pressure of oxygen at the arterial (outlet). These other blood properties were measured using a blood gas analyzer, e.g. the IL-1304 sold by Instrument Laboratories. The oxygen saturation was then calculated based on oxygen saturation curves such as those provided with the IL-1304 blood analyzer appropriate for bovine blood.

The venous and arterial oxygen saturations for each example was calculated from the results of the associated runs. The venous oxygen saturation was the calculated mean oxygen saturation of the various runs. The arterial oxygen saturation was determined by making use of the fact that a linear relationship exists between the arterial oxygen saturation and the inverse of the blood flow rate in the range of oxygen saturation levels for the defined test parameters. This is believed to result from the fact that all membrane oxygenators have a limited amount of gas exchange surface area. This limits the total level of oxygen transfer for that particular device. For each example, the best straight line relationship for the arterial oxygen saturation verse the inverse of blood flow rate was calculated using the linear least square analysis method. The maximum blood flow rate is then calculated from this linear relationship which corresponds to 100 percent arterial blood saturation.

The gas transfer rate for the oxygenator is then calculated using the following formula:

$$O_2 \text{ transfer (ml/min/m}^2\text{)} = \frac{(100\% \text{ Arterial Sat.} - \text{(mean) Venous Sat.}) \times Hb \times 1.39 \times Qb}{\text{Surface Area of transfer membrane (Meters}^2\text{)}}$$

with: Hb = hemoglobin in grams
1.39 = Oxygen capacity of 1.0 grams hemoglobin.
Qb = the maximum blood flow rate calculated as described above.

The following examples include tables of various runs indicating the measured venous oxygen saturation, calculated arterial oxygen saturation, and blood flow rate for each run.

EXAMPLE 1

Oxygenator: Bentley CM-50
Device membrane surface area: 5.6 m²

| Run | Blood Flow Liters/min. | Arterial Oxygen Saturation (%) | Venous Oxygen Saturation (%) |
|---|---|---|---|
| 1 | 2 | 100 | 44.8 |
| 2 | 4 | 96.4 | 44.4 |
| 3 | 6 | 88.4 | 43.6 |
| 4 | 8 | 83.4 | 44.0 |
| 5 | 10 | 80.4 | 44.2 |
| 6 | 12 | 79.0 | 44.0 |

The maximum blood flow rate at an arterial oxygen saturation of 100 % was calculated from the equation:

$$\text{Art. Sat. (\%)} = \frac{105.05}{\text{Maximum Blood flow}} + 70.37$$

Maximum Blood flow rate = 3.55 LPM
The mean venous oxygen saturation = 44.17%
The hemoglobin concentration = 11.5 gm %
With the oxygen transfer rate =

$$\frac{1.39 \times Hb (100 - \text{Ven. Sat.}) \times Qb \text{ (max)}}{5.6 \text{ Device Membrane Surface Area}} = 56 \frac{\text{ml (gas)/min}}{\text{square meter}}$$

EXAMPLE 2

Oxygenator: Bentley CM-50
Device membrane surface area: 5.6 m²

| Run | Blood Flow Liters/min. | Arterial Oxygen Saturation (%) | Venous Oxygen Saturation (%) |
|---|---|---|---|
| 1 | 2 | 100 | 44.9 |
| 2 | 3 | 99.5 | 44.2 |
| 3 | 4 | 95.8 | 44.2 |
| 4 | 5 | 89.8 | 44.3 |
| 5 | 6 | 86.6 | 44.7 |
| 6 | 8 | 80.9 | 44.6 |
| 7 | 10 | 78.1 | 44.6 |
| 8 | 12 | 75.6 | 44.8 |

The maximum blood flow rate at an arterial oxygen saturation of 100 % was calculated from the equation:

$$\text{Art. Sat. (\%)} = \frac{120.25}{\text{Maximum Blood flow}} + 65.93$$

Maximum Blood flow rate = 3.53 LPM
The mean venous oxygen saturation = 44.54%
The hemoglobin concentration + 11.5 gm %

With the oxygen transfer rate =

$$\frac{1.39 \times Hb \times (100 - \text{Ven. Sat.}) \times Qb \text{ (max)}}{5.6 \text{ Device Membrane Surface Area}} =$$

$$56 \frac{\text{ml (gas)/min}}{\text{square meter}}$$

EXAMPLE 3

Oxygenator: Medtronic Maxima
Device membrane surface area: 2.0 m²

| Run | Blood Flow Liters/min. | Arterial Oxygen Saturation (%) | Venous Oxygen Saturation (%) |
|---|---|---|---|
| 1 | 2 | 98.4 | 43.6 |
| 2 | 4 | 93.0 | 42.8 |
| 3 | 6 | 88.5 | 42.9 |
| 4 | 8 | 85.8 | 42.5 |
| 5 | 10 | 84.4 | 42.6 |
| 6 | 12 | 82.1 | 42.4 |

The maximum blood flow rate at an arterial oxygen saturation of 100 % was calculated from the equation:

$$\text{Art. Sat. (\%)} = \frac{72.745}{\text{Maximum Blood flow}} + 76.56$$

Maximum Blood flow rate = 3.10 LPM
The mean venous oxygen saturation = 42.90%
The hemoglobin concentration = 11.5 gm %

With the oxygen transfer rate =

-continued $$\frac{1.39 \times Hb \times (100 - Ven.\ Sat.) \times Qb\ (max)}{2.0\ \text{Device Membrane Surface Area}} =$$

$$142\ \frac{ml\ (gas)/min}{square\ meter}$$

EXAMPLE 4

Oxygenator: Medtronic Maxima
Device membrane surface area: 2.0 m²

| Run | Blood Flow Liters/min. | Arterial Oxygen Saturation (%) | Venous Oxygen Saturation (%) |
| --- | --- | --- | --- |
| 1 | 2 | 99.8 | 44.9 |
| 2 | 3 | 97.6 | 44.2 |
| 3 | 4 | 93.1 | 44.0 |
| 4 | 5 | 88.7 | 44.2 |
| 5 | 6 | 86.0 | 43.3 |
| 6 | 8 | 80.7 | 44.1 |
| 7 | 10 | 77.3 | 43.8 |
| 8 | 12 | 75.8 | 43.9 |

The maximum blood flow rate at an arterial oxygen saturation of 100 % was calculated from the equation:

$$\text{Art. Sat. (\%)} = \frac{106.33}{\text{Maximum Blood flow}} + 67.21$$

Maximum Blood flow rate = 3.24 LPM
The mean venous oxygen saturation = 44.05%
The hemoglobin concentration = 11.5 gm %

With the oxygen transfer rate =

$$\frac{1.39 \times Hb \times (100 - Ven.\ Sat.) \times Qb\ (max)}{2.0\ \text{Device Membrane Surface Area}} =$$

$$145\ \frac{ml\ (gas)/min}{square\ meter}$$

EXAMPLE 5

Oxygenator: Medtronic Maxima
Device membrane surface area: 2.0 m²

| Run | Blood Flow Liters/min. | Arterial Oxygen Saturation (%) | Venous Oxygen Saturation (%) |
| --- | --- | --- | --- |
| 1 | 2 | 100 | 44.7 |
| 2 | 3 | 99.7 | 44.7 |
| 3 | 4 | 97.9 | 44.6 |
| 4 | 5 | 93.6 | 44.6 |
| 5 | 6 | 92.1 | 44.9 |
| 6 | 8 | 87.7 | 44.8 |
| 7 | 10 | 86.6 | 45.2 |
| 8 | 12 | 84.7 | 45.2 |

The maximum blood flow rate at an arterial oxygen saturation of 100 % was calculated from the equation:

$$\text{Art. Sat. (\%)} = \frac{77.8}{\text{Maximum Blood flow}} + 78.44$$

Maximum Blood flow rate = 3.61 LPM
The mean venous oxygen saturation = 44.84%
The hemoglobin concentration = 11.5 gm %

With the oxygen transfer rate =

$$\frac{1.39 \times Hb \times (100 - Ven.\ Sat.) \times Qb\ (max)}{2.0\ \text{Device Membrane Surface Area}} =$$

$$156\ \frac{ml\ (gas)/min}{square\ meter}$$

EXAMPLE 6

Oxygenator: 3M- Sarns
Device membrane surface area: 2.2 m²

| Run | Blood Flow Liters/min. | Arterial Oxygen Saturation (%) | Venous Oxygen Saturation (%) |
| --- | --- | --- | --- |
| 1 | 2 | 100 | 44.4 |
| 2 | 3 | 99.6 | 44.6 |
| 3 | 4 | 97.4 | 44.7 |
| 4 | 5 | 93.5 | 45.1 |
| 5 | 6 | 90.6 | 44.6 |
| 6 | 8 | 86.5 | 44.8 |
| 7 | 10 | 83.7 | 45.9 |
| 8 | 12 | 82.0 | 45.4 |

The maximum blood flow rate at an arterial oxygen saturation of 100 % was calculated from the equation:

$$\text{Art. Sat. (\%)} = \frac{93.22}{\text{Maximum Blood flow}} + 74.58$$

Maximum Blood flow rate = 3.67 LPM
The mean venous oxygen saturation = 45.08%
The hemoglobin concentration = 11.5 gm %

With the oxygen transfer rate =

$$\frac{1.39 \times Hb \times (100 - Ven.\ Sat.) \times Qb\ (max)}{2.2\ \text{Device Membrane Surface Area}} =$$

$$146\ \frac{ml\ (gas)/min}{square\ meter}$$

EXAMPLE 7

Oxygenator: 3M-Sarns
Device membrane surface area: 2.2 m²

| Run | Blood Flow Liters/min. | Arterial Oxygen Saturation (%) | Venous Oxygen Saturation (%) |
| --- | --- | --- | --- |
| 1 | 2 | 99.9 | 43.9 |
| 2 | 3 | 99.1 | 43.8 |
| 3 | 4 | 95.3 | 44.9 |
| 4 | 5 | 93.2 | 43.8 |
| 5 | 6 | 89.6 | 43.8 |
| 6 | 8 | 85.1 | 43.8 |

The maximum blood flow rate at an arterial oxygen saturation of 100 % was calculated from the equation:

$$\text{Art. Sat. (\%)} = \frac{82.58}{\text{Maximum Blood flow}} + 75.49$$

Maximum Blood flow rate = 3.37 LPM
The mean venous oxygen saturation = 44.14%
The hemoglobin concentration = 11.5 gm %

With the oxygen transfer rate =

$$\frac{1.39 \times Hb \times (100 - Ven.\ Sat.) \times Qb\ (max)}{2.0\ \text{Device Membrane Surface Area}} =$$

$$137\ \frac{ml\ (gas)/min}{square\ meter}$$

EXAMPLE 8

Oxygenator: Invention

Device membrane surface area: 0.094 m²

| Run | Blood Flow Liters/min. | Arterial Oxygen Saturation (%) | Venous Oxygen Saturation (%) |
|---|---|---|---|
| 1 | 0.18 | 99.8 | 45.5 |
| 2 | 0.22 | 99.3 | 44.9 |
| 3 | 0.26 | 97.5 | 44.8 |
| 4 | 0.30 | 94.7 | 44.8 |
| 5 | 0.34 | 91.0 | 45.1 |
| 6 | 0.38 | 87.9 | 45.5 |
| 7 | 0.42 | 84.6 | 44.6 |

The maximum blood flow rate at an arterial oxygen saturation of 100 % was calculated from the equation:

$$\text{Art. Sat. (\%)} = \frac{8.78}{\text{Maximum Blood flow}} + 64.56$$

Maximum Blood flow rate = 0.25 LPM
The mean venous oxygen saturation = 45.03%
The hemoglobin concentration = 11.5 gm %

With the oxygen transfer rate =

$$\frac{1.39 \times \text{Hb} \times (100 - \text{Ven. Sat.}) \times \text{Qb (max)}}{0.094 \text{ Device Membrane Surface Area}} =$$

$$232 \frac{\text{ml (gas)/min}}{\text{square meter}}$$

EXAMPLE 9

Oxygenator: Invention
Device membrane surface area: 0.088 m²

| Run | Blood Flow Liters/min. | Arterial Oxygen Saturation (%) | Venous Oxygen Saturation (%) |
|---|---|---|---|
| 1 | 0.18 | 99.9 | 45.1 |
| 2 | 0.22 | 99.3 | 45.2 |
| 3 | 0.26 | 97.4 | 45.8 |
| 4 | 0.30 | 94.5 | 46.0 |
| 5 | 0.34 | 91.0 | 45.6 |

The maximum blood flow rate at an arterial oxygen saturation of 100 % was calculated from the equation:

$$\text{Art. Sat. (\%)} = \frac{7.00}{\text{Maximum Blood flow}} + 70.68$$

Maximum Blood flow rate = 0.24 LPM
The mean venous oxygen saturation = 45.54%
The hemoglobin concentration = 11.5 gm %

With the oxygen transfer rate =

$$\frac{1.39 \times \text{Hb} \times (100 - \text{Ven. Sat.}) \times \text{Qb (max)}}{0.088 \text{ Device Membrane Surface Area}} =$$

$$237 \frac{\text{ml (gas)/min}}{\text{square meter}}$$

EXAMPLE 10

Oxygenator: Invention
Device membrane surface area: 0.094 m²

| Run | Blood Flow Liters/min. | Arterial Oxygen Saturation (%) | Venous Oxygen Saturation (%) |
|---|---|---|---|
| 1 | 0.18 | 99.8 | 45.2 |
| 2 | 0.22 | 99.1 | 44.9 |
| 3 | 0.26 | 97.0 | 44.7 |
| 4 | 0.30 | 93.8 | 44.9 |
| 5 | 0.34 | 91.5 | 44.9 |
| 6 | 0.38 | 88.1 | 45.9 |

The maximum blood flow rate at an arterial oxygen saturation of 100 % was calculated from the equation:

$$\text{Art. Sat. (\%)} = \frac{7.09}{\text{Maximum Blood flow}} + 70.00$$

Maximum Blood flow rate = 0.24 LPM
The mean venous oxygen saturation = 45.08%
The hemoglobin concentration = 11.5 gm %

With the oxygen transfer rate =

$$\frac{1.39 \times \text{Hb} \times (100 - \text{Ven. Sat.}) \times \text{Qb (max)}}{0.094 \text{ Device Membrane Surface Area}} =$$

$$221 \frac{\text{ml (gas)/min}}{\text{square meter}}$$

As demonstrated from the above Examples, as better illustrated in the following Table 1, the gas exchange efficiency of an oxygenator constructed in accordance with the invention was greater than the efficiency of gas exchange achieved by other oxygenators. Specifically, the device of the invention provides for oxygen transfer of about 230 milliliters per minute per fiber surface area, whereas, only the 3M-Sarns and Medtronic Maxima oxygenators achieved an oxygen transfer of at best 146 and 156 milliliters per minute per fiber surface area, respectively.

As also seen in Table 1, the overall priming volume of the device of the invention is smaller due to the better gas efficiency obtained with a lower gas exchange membrane surface area. That is, the overall surface area is significantly lower, with the oxygenator of the invention, thus reducing the overall size and thus priming volume. Any reduction in priming volume is advantageous.

| DEVICE TYPE | INVENTION[1] | BENTLEY | 3M-SARNS | MEDTRONIC |
|---|---|---|---|---|
| AVERAGE O₂ TRANSFER (ml/min/m2) | 230 | 56 | 142 | 148 |
| MAX. O₂ TRANSFER (ml/min/m²) | 237 | 56 | 146 | 156 |
| BLOOD PRESSURE DROP AT 7 LPM (mm Hg) 80 | | 120[1] | 230 | 180 |
| fiber surface area (m²) | 1.4[1] | 5.6 | 2.2 | 2.0 |
| Device Priming Volume (ml) | 200[1] | 730 | 320 | 480 |

[1]Values projected for the device of the invention which is capable of generating a total oxygen transfer of 320 ml/min. The values from the above experiments were extrapolated to achieve these results.

The configuration of the oxygenator of the invention may be modified to provide for other equivalent embodiments. For example, the bellows can be modified to position the blood receiving channels across its length, that is running from one end to the other. The bellow pleats of this embodiment would be generally orientated at 90° to the pleats in the above discussed and illustrated embodiment. The fiber bundles would be arranged between adjacently positioned pleats, with gas and blood manifolds secured to each of the bellow ends.

In another embodiment the cylindrical bellows 14 would be replaced by a relatively flat core or blood flow pathway defining structure. That is, the device would include a flat corrugated structure positioned within a housing. Bundles of hollow fibers would be positioned between the corrugations to form a gap between the fiber bundles and the outer surface of the corrugated structure. These fibers would be potted at the opposite ends of the structure to expose the fiber open ends. A gas manifold would be positioned about these opposite ends to direct gas through the fibers. A blood manifold would deliver blood between the corrugations into the formed gaps. The blood would flow out through the bundles of fibers once the gaps became substantially filled.

While the preferred embodiments have been described and illustrated, various modifications and substitutions may be made thereto without departing from the scope of the invention. Accordingly, it is to be understood that the invention has been described by way of illustration and not limitation.

What is claimed is:

1. A blood oxygenator comprising:
   a housing formed with a blood outlet, a gas inlet and a gas outlet;
   a cylindrical support core having an outer surface and contained within the housing;
   a cylindrically shaped bellows having a plurality of pleats defining a plurality of blood receiving channels, said cylindrically shaped bellows having an outer wall disposed about the outer surface of the core;
   means communicating with the cylindrically shaped bellows for delivering blood to each of the blood receiving channels;
   a plurality of gas permeable hollow fiber membranes positioned in each of the blood receiving channels, each of the hollow fiber membranes having a first open end in communication with the gas inlet and an opposing second open end in communication with the gas outlet; wherein a gas enters each hollow fiber membrane through the first open end and exits at the second open end; and
   a plurality of circumferential and uninterrupted blood flow passageways within the blood receiving channels, the blood flow passageways defined between the outer wall of the cylindrically shaped bellows and the plurality of hollow fiber membranes, the blood flow passageways in fluid communication with the blood outlet.

2. The device of claim 1 wherein the gas permeable hollow fiber membranes fill from about 40 to about 60 percent of each respective channel.

3. The device of claim 1, wherein the blood receiving channels are defined between adjacently positioned pleats.

4. The device of claim 3, wherein the blood delivery means is a blood manifold.

5. The device of claim 4, wherein the blood manifold is an elongated body mounted to the bellows, the blood manifold formed with a first main conduit and a plurality of fingers extending outwardly from the body and each positioned in a respective one of the blood receiving channels and communicating therewith, the plurality of fingers including at least one finger passage communicating with the first main conduit, wherein blood delivered from the first main conduit enters the blood receiving channels through the at least one finger passage.

6. The device of claim 5, wherein each of the first open ends of the hollow fiber membranes are arranged in a first column and each of the second open ends of the hollow fiber membranes are arranged in a second column, the first and second columns positioned side by side along the bellows.

7. The device of claim 6, wherein the first open ends and the second open ends of the hollow fiber membranes are embedded within a potting material.

8. The device of claim 6, further comprising a gas manifold having a first chamber aligned with the first column and a second chamber aligned with the second column, wherein the first and second chambers are separated by a partition wall.

9. The device of claim 1, further comprising a blood exit manifold integrally connected to the housing for collecting blood passing through the plurality of hollow fiber membranes.

10. The device of claim 1, wherein the plurality of hollow fiber membranes are arranged in each of the blood receiving channels to define spacings between adjacently positioned ones of the hollow fiber membranes through which blood may flow, and wherein blood delivered from the blood delivering means flows uninterruptedly through the blood flow passageways and substantially fills the blood flow passageways before passing outwardly in a radial direction through the spacings between the hollow fiber membranes.

11. A blood oxygenator comprising:
    a housing formed with a gas inlet and a gas outlet;
    a cylindrical support core contained within the housing;
    a cylindrically shaped bellows mounted within the housing and about the core, the bellows having an outer wall with a plurality of pleats formed therein, with a plurality of blood receiving channels being defined between adjacently positioned pleats and the outer wall;
    a blood manifold communicating with the bellows for delivering blood to each of the blood receiving channels;
    a plurality of gas permeable hollow fiber membranes positioned in each of the blood receiving channels, each of the hollow fiber membranes having a first open end in communication with the gas inlet and an opposing second open end in communication with the gas outlet; wherein a gas enters each hollow fiber membrane through the first open end and exits at the second open end, and wherein the plurality of hollow fiber membranes are arranged in each of the blood receiving channels to defined spacings between adjacently positioned ones of the hollow fiber membranes through which blood may flow;
    a plurality of circumferential and uninterrupted blood flow passageways positioned within the blood receiving channels, the blood flow passageways defined between the outer wall of the bellows and the plurality of hollow fiber membranes, wherein blood delivered from the blood manifold flows uninterruptedly through the blood flow passageways and substantially fills the blood flow passageways before passing outwardly in radial direction through the spacings between the hollow fiber membranes; and a blood exit manifold integrally connected to the housing for collecting blood passing through the spacings between the plurality of hollow fiber membranes.

12. The device of claim 11, wherein the blood manifold is an elongated body mounted to the bellows, the blood manifold formed with a first main conduit and a plurality of fingers extending outwardly from the body and each positioned in a respective one of the blood receiving channels and communicating therewith, the plurality of fingers including at least one finger passage communicating with the first main conduit, wherein blood delivered from the first main conduit enters the blood receiving channels through the at least one finger passage.

13. The device of claim 12, wherein each of the first open ends of the hollow fiber membranes are arranged in a first column and each of the second open ends of the hollow fiber membranes are arranged in a second column, the first and second columns positioned side by side along the bellows.

14. The device of claim 13, wherein the first open ends and the second open ends of the hollow fiber membranes are embedded within a potting material.

15. The device of claim 10, further comprising a first horizontal blood flow path defined by the blood delivering means and the blood flow passageways.

16. The device of claim 15, further comprising a second radial blood flow path defined by the spacings between the plurality of hollow fiber membranes.

* * * * *